United States Patent [19]

Kaplan et al.

[11] Patent Number: 4,732,157

[45] Date of Patent: Mar. 22, 1988

[54] METHOD AND APPARATUS FOR QUANTIFYING BEAT-TO-BEAT VARIABILITY IN PHYSIOLOGIC WAVEFORMS

[75] Inventors: Daniel T. Kaplan, Cambridge; Richard J. Cohen, Newton Highlands, both of Mass.

[73] Assignee: Massachusetts Institute of Technology, Cambridge, Mass.

[21] Appl. No.: 897,602

[22] Filed: Aug. 18, 1986

[51] Int. Cl.$^4$ .............................................. G01R 23/02
[52] U.S. Cl. ................................... 128/696; 128/702; 128/703; 128/704; 364/417; 364/421; 364/500
[58] Field of Search ............... 128/696, 702, 703, 704; 364/417, 421, 500, 518, 555

[56] References Cited

U.S. PATENT DOCUMENTS

| | | | |
|---|---|---|---|
| 4,375,079 | 2/1983 | Ricketts et al. | 364/518 |
| 4,453,226 | 6/1984 | Hobbs et al. | 364/555 |
| 4,463,425 | 7/1984 | Hirano et al. | 128/704 |
| 4,543,632 | 9/1985 | Ergas et al. | 364/421 |
| 4,633,400 | 12/1986 | Chittineni | 364/421 |
| 4,661,913 | 4/1987 | Wu et al. | 364/500 |

OTHER PUBLICATIONS

"Ventricular Fibrillation and Fluctuations in the Magnitude of the Repolarization Vector"; D. R. Adam et al., IEEE Comp. Soc. reprint; 1982, Comp in Card pp. 241/244.

"Estimation of Ventricular Vulnerability to Fibrillation Through T-Wave Time Series Analysis"; D. R. Adam et al., Comp. in Card., Sep. 1981, pp. 307–310.

"Fluctuations in T-Wave Morphology and Susceptibility to Ventricular Fibrillation"; D. R. Adam et al., J. Electrocard. 17(3) 1984, pp. 209–218.

*Primary Examiner*—William E. Kamm
*Assistant Examiner*—Timothy Keegan

[57] ABSTRACT

Myocardial electrical stability is assessed by sampling an ECG waveform at corresponding fiducial locations for a plurality of beats and creating a scatter plot of the $i^{th}$ sample versus the $(i-1)$th sample. A parameter $\lambda$ is determined which minimizes the sum of the total distances of the points of the scatter plot to an equation $x(i)=4\lambda x(i-1)[1-x(i-1)]$. The value of the parameter $\lambda$ is related to the electrical stability of the heart.

19 Claims, 2 Drawing Figures

METHOD AND APPARATUS FOR QUANTIFYING BEAT-TO-BEAT VARIABILITY IN PHYSIOLOGIC WAVEFORMS

The Government has rights in this invention pursuant to Contract Number N00014-80-C-0520 awarded by the Department of the Navy.

BACKGROUND OF THE INVENTION

This invention relates to method and apparatus for characterizing variability in physiologic waveforms, and more particularly to assessing myocardial electrical stability from an ECG waveform.

Sudden cardiac death, defined as death resulting from cardiac cause within 24 hours of onset of symptoms, has been referred to as the most challenging problem facing contemporary cardiology. Most sudden deaths are unexpected, unheralded by symptoms of any duration or by overt coronary artery disease. In the United States alone, sudden cardiac death typically claims between 400,000 and 500,000 lives each year, and represents the major cause of death for men between the ages of 20 and 64.

It is thought that the mechanism responsible for the great majority of sudden cardiac deaths is ventricular fibrillation, a state in which the normally organized electrical activity of the heart becomes disorganizes and apparently chaotic. This disorganized electrical activity initiates similarly disorganized and ineffectual mechanical contraction of the pumping chambers of the heart resulting in circulatory collapse and death.

By far the most desirable and potentially the most effective response to the problem of sudden cardiac death is prevention, in which the first step would necessarily be the identification of those individuals at increased risk. It is this identification with which the present invention is concerned.

One non-invasive technique for assessign the "cardiac status" of a given individual involves analysis of the alternation from beat-to-beat in the morphology of the electrocardiogram (ECG) complex. While it has been long hypothesized that a link exists between alternation in ECG morphology and myocardial electrical stability, the prior art techniques have been only marginally successful. The prior art comprehends the relationship of fluctuations in the T-wave morphology of the ECG complex with susceptibility to ventricular fibrillation. See, for example, "Fluctuations in T-Wave Morphology and Susceptibility to Ventricular Fibrillation," by Adam et al. in the *Journal of Electrocardiology* 17 (3), 1984, 209-218; "Estimation of Ventricular Vulnerability to Fibrillation Through T-Wave Time Series Analysis" by Adam et al., *Computers in Cardiology*, September 1981; "Ventricular Fibrillation and Fluctuations in the Magnitude of the Repolarization Vector," by Adam et al., IEEE, 1982 Computers in Cardiology. In these references, the alternation of T-wave energy from beat-to-beat was measured to generate a T-wave alternation index (TWAI). This technique, however, is unable to detect alternation in waveform morphology which results in alternating wave shapes of equal energy. Additionally, the amount of alternation detected was dependent on the specific static portion wave shape. Thus, the same amount of alternation superimposed on a different amplitude signal resulted in different values for the T-wave alternation index. This technique might even completely obscure the presence of alternation in the original waveform morphologies.

This technique is furthermore very sensitive to the presence of both measurement and/or forcing noise. Measurement noise can result from skeletal muscle activity or other environmental sources unrelated to the signal being measured. Forcing noise occurs from perturbations to the signal itself (in the case of the ECG, forcing noise may result from nervous system modulation of cardiac conduction processes, ventricular premature beats, etc.).

In a pending U.S. patent application Ser. No. 897,603 of one of the applicants herein, method and apparatus is disclosed and claimed for analyzing a physiologic waveform such as the ECG in which sample point matrices are constructed from the digitized waveform signal. Variability in the waveform is determined by operations on the columns of the sample point matrices. This technique has been used to generate an alternating ECG morphology index which has a high correlation of decreased ventricular fibrillation threshold with increases in the alternating ECG morphology index.

It is an object of the present invention to provide a novel method for quantifying cycle-to-cycle variation in a physiologic waveform such as the ECG.

It is another object of the invention to derive a numerical parameter from a physiologic waveform which is associated with susceptibility to ventricular fibrillation.

SUMMARY OF THE INVENTION

These and other objects of the invention are accomplished by sampling a physiologic waveform at corresponding fiducial locations for a plurality of cycles and creating for a fixed fiducial point offset a scatter plot of the sample taken of the ith cycle versus the sampe of the (i−1)th cycle. A parameter $\lambda$ is determined which optimizes the fit of the scatter plot to an equation $x(i)=4\lambda x(i-1)[1-x(i-1)]$. Here the x(i) represents a linear transformation of the sample points y(i). The value of the parameter $\lambda$ is associated with the susceptibility of the physiologic waveform to enter into an aperiodic or chaotic state.

DESCRIPTION OF THE PREFERRED EMBODIMENT

Period doubling has been observed in ECG's of experimental animals with high susceptibility to fibrillation as measured by the ventricular fibrillation threshold (VFT) test. Period doubling represents an excitation of a system at the first subharmonic of its fundamental frequency. In the context of the ECG it represents a modulation of the ECG waveform occurring on an every other beat basis "electrical alternans". Previous efforts at detecting doubling have utilized spectral techniques to measure the amount of waveform variability at the period doubling frequency.

It has been recognized that the period doubling phenomena (and other higher order periodicities may result from a nonliner autoregressive process which can also lead to chaotic aperiodic regimens (Feigenbaum, M. J., "Universal Behavior In Nonlinear Systems", *Los*

Alamos Science 1:4, 1980). One simple nonlinear autoregressive operator which displays this behavior is $x(i)=4\lambda x(i-1)[1-x(i-1)]$. The parameter $\lambda$ varies from 0 to unity and determines the strength of the coupling between $x(i-1)$ and $x(i)$ and also determines the periodicity of the behavior. In the method of this invention the linearly transformed sample points $x(i)$ are fitted to the above equation and the strength of the coupling $\lambda$ is determined. This measurement is much less sensitive to noise than is the case with spectral techniques. The expected periodicity could be effected by noise, yet $\lambda$ could still be accurately determined. Measurement of $\lambda$ thus enables one to characterize the underlying beat-to-beat coupling which leads to both the periodic behavior and chaotic behavior. Measurement of $\lambda$ may provide an index of ECG waveform variability which may provide an improved correlation with susceptibility to ventricular fibrillation than previously available indices.

Figure 1:
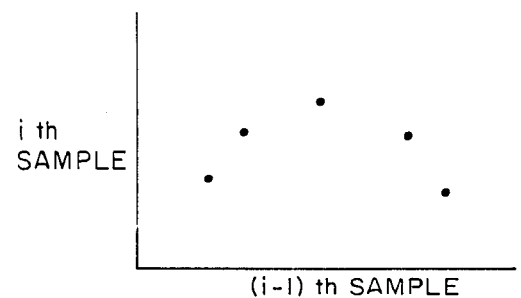
FIG. 1 is a scatter plot of the ith sample versus the (i−1)th sample.

The technique disclosed herein involves sampling an ECG or other physiologic waveform at corresponding fiducial locations for a series of cycles of the waveform. For example, when the ECG is the physiologic waveform, the ECG is sample at equal intervals after the peak of the QRS complex. It is to be understood that other portions of the ECG waveform may be utilized. the sampling operation generates a number for each beat in the ECG which represents the value of the ECG at the fiducial location. A scatter plot is made of the ith sample versus the $(i-1)$th sample. Of course, it is not necessary to create an actual graph of the data points. What would be stored are the ordered pairs for the ith and $(i-1)$th samples. FIG. 1 shows a representation scatter plot of the ith sample value versus the $(i-1)$th sample value. The exemplary data shown in FIG. 1 are fitted to the equation $x(i)=4\lambda x(-1)[1-x(i-1)]$ using an iterative method to determine the value of $\lambda$ which minimizes the sum of the total distances of the points to the curve. The single parameter $\lambda$ is used to quantify the degree of alternation in the sampled waveform.

The above equation has been much studied in the context of strange attractors and the transition to chaos of dynamical systems. For systems described by this equation, period doubling is observed for $0.75<\lambda<0.87$. As $\lambda$ is increased further, a cascade of period doublings is observed. This cascade terminates in an aperiodic (chaotic) system for $\lambda$ greater than 0.89. It has been shown that many dynamic systems behave similarly to the above equation as the chaotic limit is approached. In this sense, $\lambda$ can be used to measure how close a system is to chaos.

Figure 2:
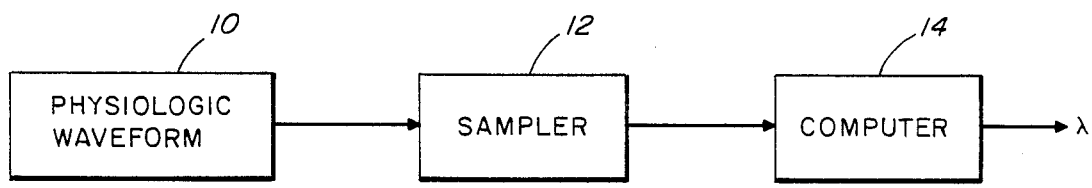
FIG. 2 is a schematic block diagram of an implementation of the present invention.

FIG. 2 shows a physical implementation of the present technique. The physiologic waveform, for example, an ECG is recorded, block 10, and sample in the sampler 12. As discussed above, sampling may be performed at equal intervals after the peak of the QRS complex of an ECG. The output of the sampler 12 is stored in a computer 14 which uses an iterative method to minimize the sum of the total distances of the sample points to the curve described by the above set forth equation. The output of the computer 14 is the parameter $\lambda$.

As stated above, period doubling in an ECG is correlated with high susceptibility to fibrillation as measured by the ventricular fibrillation threshold test. The above set-forth equation exhibits period doubling when $\lambda$ exceeds 0.75. Therefore, a value of $\lambda$ exceeding 0.75 indicates high susceptibility to fibrillation. This technique may also be utilized with other physiologic waveforms such as blood pressure and respiration waveforms.

It is recognized that modifications and variations of the present invention will be apparent to those skilled in the art and it is intended that all such modifications and variations be included within the scope of the appended claims.

What is claimed is:

1. Method for determining cycle-to-cycle alternation in a physiologic waveform comprising:
    sampling the waveform at corresponding fiducial locations for a plurality of cycles;
    creating a scatter plot of the ith sample versus the $(i-1)$th sample; and
    determining a parameter $\lambda$ which optimizes the fit of the scatter plot to an equation $x(i)=4\lambda x(i-1)[1-x(i-1)]$, the value of $\lambda$ quantifying the degree of alternation.

2. The method of claim 1 using an iterative method to determine $\lambda$.

3. The method of claim 1 wherein the physiologic waveform is the ECG.

4. The method of claim 1 wherein the physiologic waveform is a blood pressure waveform.

5. The method of claim 1 wherein the physiologic waveform is a respiratory waveform.

6. The method of claim 3 wherein the fiducial location is beyond the peak of the QRS complex of the ECG.

7. Method for assessing susceptibility to ventricular fibrillation comprising:
    sampling an ECG waveform at corresponding fiducial locations for a plurality of beats;
    creating a scatter plot of the ith sample versus the $(i-1)$th sample; and
    determining a parameter $\lambda$ which minimizes the sum of total distances of the points of the scatter plot to an equation $x(i)=4\lambda x(i-1)[1-x(i-1)]$, the value of the parameter $\lambda$ being related to the susceptibility of fibrillation.

8. The method of claim 7 wherein a value of $\lambda$ greater than 0.75 indicates high susceptibility to fibrillation.

9. Apparatus for determining cycle-to-cycle alternation in a physiologic waveform comprising:
    means for sampling the waveform at corresponding fiducial locations for a plurality of cycles;
    means for creating a scatter plot of the ith sample versus the $(i-1)$th sample; and
    computing means for determining a parameter $\lambda$ which minimizes the sum of the total distances of the points of the scatter plot to an equation $x(i)=4\lambda x(i-1)[1-x(i-1)]$, the value of $\lambda$ quantifying the degree of alternation.

10. The apparatus of claim 9 wherein the computing means utilizes an iterative method to determine $\lambda$.

11. The apparatus of claim 9 wherein the physiologic waveform is the ECG.

12. The apparatus of claim 9 wherein the physiologic waveform is a blood pressure waveform.

13. The apparatus of claim 9 wherein the physiologic waveform is a respiratory waveform.

14. The apparatus of claim 11 wherein the fiducial location is beyond the peak of the QRS complex of the ECG.

15. Apparatus for assessing susceptibility to ventricular fibrillation comprising:
    means for sampling an ECG waveform at corresponding fiducial locations for a plurality of beats;

means for creating a scatter plot of the ith sample versus the (i−1)th sample; and computing means for determining a parameter $\lambda$ which minimizes the sum of total distances of the points of the scatter plot to an equation $x(i)=4\lambda x(i-1)[1-x(i-1)]$, the value of the parameter $\lambda$ being related to the susceptability to fibrillation.

16. The apparatus of claim 15 wherein a value of $\lambda$ greater than 0.75 indicates high susceptibility to fibrillation.

17. Method for assessing susceptibility to ventricular fibrillation comprising:

sampling a physiologic waveform at corresponding fiducial locations for a plurality of cycles;

creating a scatter plot of the ith sample versus the (i−1)th sample; and determining a parameter $\lambda$ which minimizes the sum of total distances of the points of the scatter plot to an equation $x(i)=4\lambda x(i-1)[1-x(i-1)]$, the value of the parameter $\lambda$ being related to the susceptibility to fibrillation.

18. Apparatus for assessing susceptibility to ventricular fibrillation comprising:

means for sampling a physiologic waveform at corresponding fiducual locations for a plurality of beats;

means for creating a scatter plot of the ith sample versus the (i−1)th sample; and computing means for determining a parameter $\lambda$ which minimizes the sum of total distances of the points of the scatter plot to an equation $x(i)=4\lambda x(i-1)[1-x(i-1)]$, the value of the parameter $\lambda$ being related to the susceptibility to fibrillation.

19. Method for determining cycle-to-cycle alternation in a physiologic waveform comprising:

sampling the waveform at corresponding fiducial locations for a plurality of cycles;

storing ordered pairs for the ith and (i−1)th samples; and determining a parameter $\lambda$ which minimizes the sum of the total distances of the points represented by the ordered pairs to an equation $x(i)=4\lambda x(-1)[1-x(i-1)]$, the value of $\lambda$ quantifying the degree of alternation.

* * * * *

UNITED STATES PATENT AND TRADEMARK OFFICE
CERTIFICATE OF CORRECTION

PATENT NO. : 4,732,157
DATED : March 22, 1988
INVENTOR(S) : Daniel T. Kaplan and Richard J. Cohen It is certified that error appears in the above-identified patent and that said Letters Patent are hereby corrected as shown below:

```
Column 1, line 29, "disorganizes" should be --disorganized--;
         line 40, "assessign" should be --assessing--.

Column 3, line 24, "sample" should be --sampled--;
         line 27, "the" should be --The--;
         line 33, "representation" should be
--representative--;
         line 35, "are" should be --is--;
         line 36, (-1)" should be --(i-1)--;
         line 54 "sample" should be --sampled--.

Column 6, line 21, "(-1)" should be --(i-1)--.
```

Signed and Sealed this

Twelfth Day of July, 1988

Attest:

DONALD J. QUIGG

Attesting Officer

Commissioner of Patents and Trademarks